United States Patent [19]

Mussi et al.

[11] Patent Number: 5,409,829
[45] Date of Patent: Apr. 25, 1995

[54] DEVICE FOR TRANS-MEMBRANE CO-CULTURE OF CELLS AND A METHOD FOR USING SAME

[75] Inventors: Edward F. Mussi, Hewitt; Harry E. Gray, Bloomingdale, both of N.J.

[73] Assignee: Becton, Dickinson and Company, Franklin Lakes, N.J.

[21] Appl. No.: 124,415

[22] Filed: Sep. 21, 1993

[51] Int. Cl.$^6$ .......................... C12N 5/00; C12M 3/06
[52] U.S. Cl. ............................................. 435/240.241
[58] Field of Search ................................. 435/284–287, 435/296, 298–301, 310, 311, 810, 240.241; 422/99, 101, 102

[56] References Cited

U.S. PATENT DOCUMENTS

| | | | |
|---|---|---|---|
| 4,871,674 | 10/1989 | Matsui et al. | 435/284 |
| 4,959,197 | 9/1990 | Pareka et al. | 422/101 |
| 5,026,649 | 6/1991 | Lyman et al. | 422/101 |
| 5,272,083 | 12/1993 | Butz et al. | 422/101 |

FOREIGN PATENT DOCUMENTS 9015862  12/1990  WIPO .

OTHER PUBLICATIONS

Magnum et al., In Vitro Cell Dev. Biol., 26:1135–1143 (Dec. 1990).
Madara et al. J. Tissue Cult. Method 14:209–216 (1992).
Grobstein, "Trans Filter Induction of Tubules in Mouse Metanephrogenic Mesenchyme", Experimental Cell Research, vol. 10 (1956) pp. 424–440.

*Primary Examiner*—William H. Beisner
*Attorney, Agent, or Firm*—Arthur D. Dawson

[57] ABSTRACT

A self-contained ready-to-use trans-membrane co-culture system of the present invention includes an insert having a tube with a longitudinal axis, a sidewall substantially parallel to the axis connecting a first open end and a second end. The second end has a microporous membrane bonded to it substantially perpendicular to the axis forming a well within the insert. The insert has a flange extending outwardly from the sidewall at the first end for suspending the insert as described hereinabove with a removable plug placed in the well of the insert to substantially prevent fluid flow through the microporous membrane. The insert with the plug is contained in a housing having a first end, a second end and a passageway therethrough. The housing has a longitudinal axis, a first diameter at the first end, a second diameter at the second end and an intermediate diameter between the first and second diameter. When the second end of the insert is coaxially placed in the first end of the housing, the second end of the insert has an interference fit with the intermediate diameter of the housing forming a chamber above the microporous membrane. The first and second ends of the housing are reclosably sealed with gas permeable lids that substantially prevent the passage of microorganisms into the sterililzed system housing as long as the lids are unopened. The present invention includes a method for trans-membrane co-culture of cells using the insert and the system of the present invention.

11 Claims, 4 Drawing Sheets

DEVICE FOR TRANS-MEMBRANE CO-CULTURE OF CELLS AND A METHOD FOR USING SAME

FIELD OF INVENTION

This invention generally relates to the trans-membrane co-culture of cells. More particularly the invention relates to a cell-culture insert with a microporous membrane, a system incorporating the insert and a method for its use in culturing cells.

BACKGROUND OF THE INVENTION

Culturing of cells of various types has become a routine process in many laboratories. Cells are grown to harvest compounds, to test for various sensitivities to potentially toxic compounds and even to provide tissue for gratis. More recently, cells of different types have been co-cultured on opposite sides of a microporous membrane for the study of interactions between one type of cell and another, particularly in the study of inflammatory responses.

Representative references to the co-culture of cells include: Magnum et al., *In Vitro Cell Dev. Biol.* 26:1135–1143 (Dec., 1990) describe a "Co-Culture of primary Pulmonary Cells to Model Alveolar Injury and Translocation of Protein"; and Madara et al. in *J. Tissue Cult. Method.* 14:209–216, (1992) report "A Simple Approach to Measurement of Electrical Parameters of Cultured Epithelial Monolayers: Use in Assessing Neutrophil-Epithelial Interactions." Both of these papers with the references therein, hereby incorporated by reference, report a technique for growing cells of two different types on opposite sides of a suspended microporous membrane. Madara et al. provide a detailed report of a trans-membrane co-culture study. Madara et al. also describe modifications of a commercial cell culture insert by adhesively bonding a machined polycarbonate ring onto the underside of the insert to facilitate the growth of monolayers on both sides of the membrane. These modifications of an existing product described by Madara et al., provided them with a way to conduct an experiment. However, adhesively bonding separate rings on to the bottoms of cell inserts is both tedious and a potential source of leachable materials from the adhesive. Additionally, researchers using devices assembled from modified existing parts likely spend nearly as much time modifying the devices as they do conducting their studies, thus reducing their productivity. The modified devices generally do not have the refinements that a purpose built item can incorporate after an analysis of needs and problems, further inhibiting productivity. Since there is increasing interest in the study of cellular interactions, there is a need for a ready-to-use trans-membrane co-culture system to facilitate the research in this area.

SUMMARY OF THE INVENTION

The present invention provides the art of cell co-culture with a substantially sterile ready-to-use system for co-culture of cells. A worker using the present invention may proceed directly to growing initial and secondary cells without concerns about cyto-toxic extractables, cross-contamination and wild strains of microorganisms interfering with the study.

A trans-membrane co-culture insert of the present invention includes a tube that has a passageway therethrough with a longitudinal axis. The tube has a first open end connected to a second end by a sidewall substantially parallel to the axis. A microporous membrane is bonded to the second end substantially perpendicular to the axis to close the second end and form a well within the insert. A flange extends outwardly from at least a portion of the sidewall at the first end. The flange is substantially perpendicular to the axis and may be used for suspending the insert in a standard cell culture well plate.

A self-contained trans-membrane co-culture system of the present invention includes an insert as described herein above contained in a housing. The system further includes a removable plug, sized and placed to fit with an interference within the well of the insert to substantially obstruct fluid flow through the microporous membrane.

The housing contains the insert with the plug therein. The housing is an open tube with a first end, a second end and a passageway therethrough. The housing has a longitudinal axis, a first diameter at the first end, a second diameter at the second end and an intermediate diameter between the first and second ends. The diameter at the first end of the housing is larger than the insert second diameter. The housing intermediate and second diameters are less than the insert second end diameter. The housing first end has a flange extending outwardly substantially perpendicular to the housing longitudinal axis that forms a surface. The housing second end has a lip extending inwardly substantially perpendicular to the housing axis forming a surface having an opening therethrough about the axis. A chamber with a substantially fluid tight fit is formed at the housing intermediate diameter by coaxial placement of the second end of the insert into the first end of the housing. The flange on the insert is contained within the housing at the housing first end. The first end of the housing is substantially sealed by a reclosable first lid peelably bonded to the first surface and the second end of the housing is substantially sealed by a reclosable second lid peelably bonded to the second surface.

A method for trans-membrane co-culture of cells includes providing a trans-membrane co-culture system as described hereinabove and orienting it with the first end down and the second end up. The method then includes peeling the second lid open and exposing the chamber, adding to the chamber a mixture containing the initial cells to be grown in a sufficient quantity of a suitable growth medium; reclosing the second lid; and placing the system in an environment suitable for cell growth. The method further includes removing the second lid, removing the growth medium leaving the initial cells on the membrane; inverting the system; and removing the first lid. The method then includes withdrawing the insert from the housing; removing the plug from the insert; and providing a well plate that has a well suitable for suspending the insert. The method then includes placing a suitable growth medium in the well of the plate; suspending the insert into the well of the plate by the flange so that the growth medium contacts the membrane with the initial cells on its surface; adding a mixture with secondary cells to be grown in a sufficient quantity of a suitable medium to the well of the insert; and placing the plate with the insert suspended therein in a suitable environment for cell growth and allowing the cells to grow.

DETAILED DESCRIPTION OF THE PREFERRED EMBODIMENTS

Figure 1:
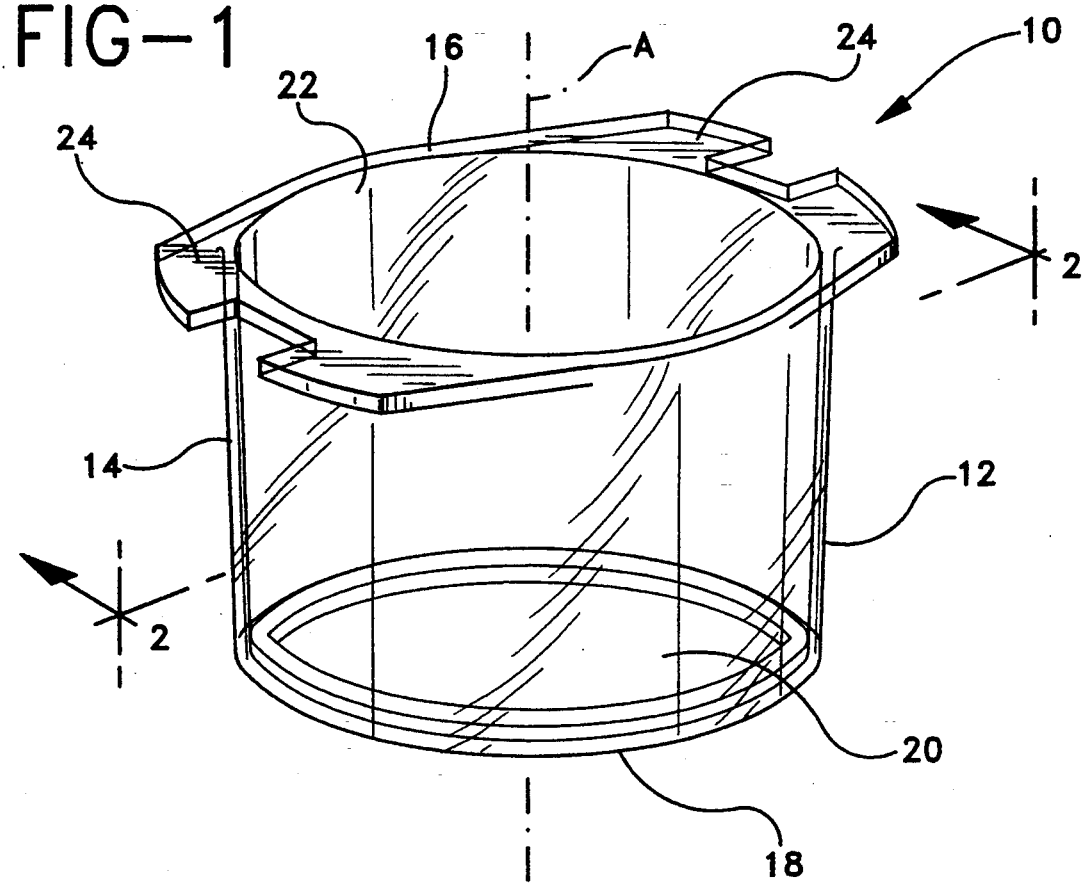
FIG. 1 is a perspective view of a cell-culture insert of the present invention.
Figure 2:
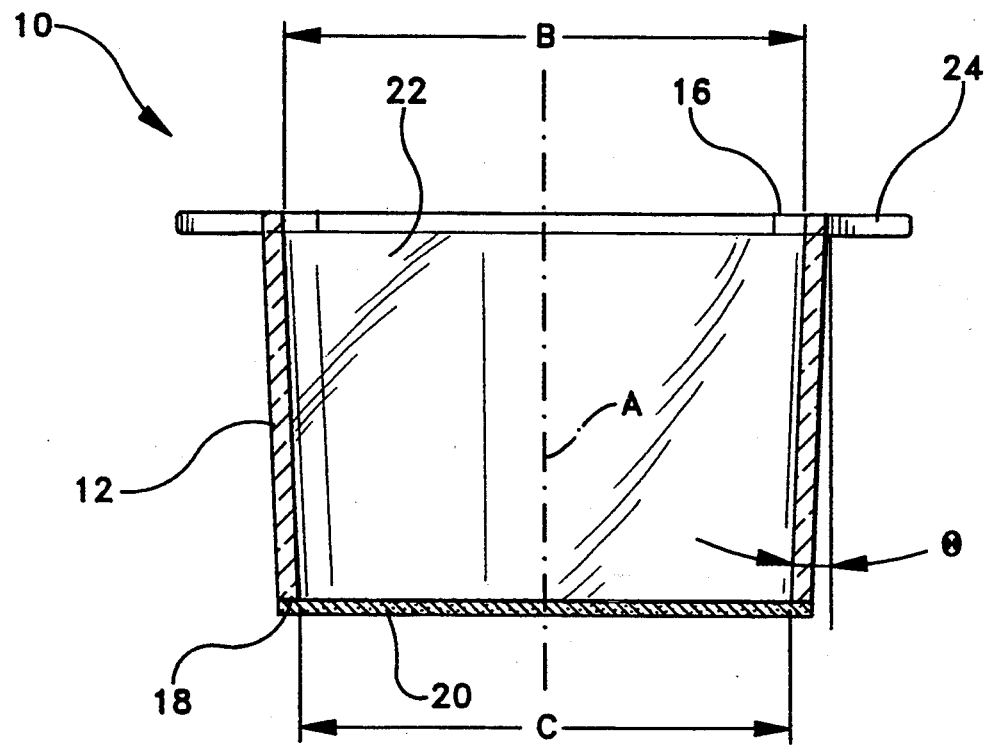
FIG. 2 is a cross-sectional view of the insert of the present invention illustrated in FIG. 1, taken along the line 2,2.

While this invention is satisfied by embodiments in many different forms, there will be described herein in detail, preferred embodiments of the invention, with the understanding that the present disclosure is to be considered as exemplary of the principles of the invention and is not to be intended to limit the invention to the embodiments described. The scope of the invention will be measured by the appended claims and their equivalents.

Referring to the drawings FIGS. 1–4, a trans-membrane co-culture insert 10 includes a tube with a longitudinal axis "A". The tube has a sidewall 14 substantially parallel to axis "A" connecting a first open end 16 and a second end 18. Second end 18 has a microporous membrane bonded thereto substantially perpendicular to axis "A" closing second end 18 and forming a well 22 within the insert. First end 16 has a flange 24 extending outwardly from at least a portion of sidewall 14. Flange 24 is substantially perpendicular to axis "A" and is useful for suspending insert 10 in a well in many standard commercial cell culture well plates. Tube 12 preferably is a frustum of a cone with a first diameter "B" at first end 16 and a second diameter "C" at second end 18. Diameter "B" is larger than diameter "C" so that sidewall 14 preferably forms an angle Θ from parallel to axis "A" of less than about 10°.

Preferably, sidewall 14 is substantially rigid and may be formed from a polymeric material such as polyethylene terephthalate, polyethylene, polycarbonate, polystyrene and the like. Polyethylene terephthalate (Eastman 7352, Kingsport, Tex.) is preferably injection molded to form the sidewall.

Microporous membrane 20 may be formed from a polymeric material such as polyethylene terephthalate, polycarbonate and the like with open pores therethrough. Preferably, the membrane is between about 20 to about 30 microns thick and the pores are between about 0.2 to about 10 microns in diameter with a pore density between about $0.1 \times 10^6$ to about $10.0 \times 10^6$ pores per square centimeter. Membrane 20 may be bonded to second end 18 by adhesive bonding, solvent bonding, ultrasonic welding, thermal bonding or any other method for providing a secure attachment between the sidewall and the membrane. Preferred materials for the microporous membrane are available from "Cyclopore" (Avenue Einstein, Louvain-la-Neuve, Belgium) and "Poretics" (Livermore, Calif.). Preferably, membrane 20 is bonded to the second end by Solvent bonding.

Figure 3:
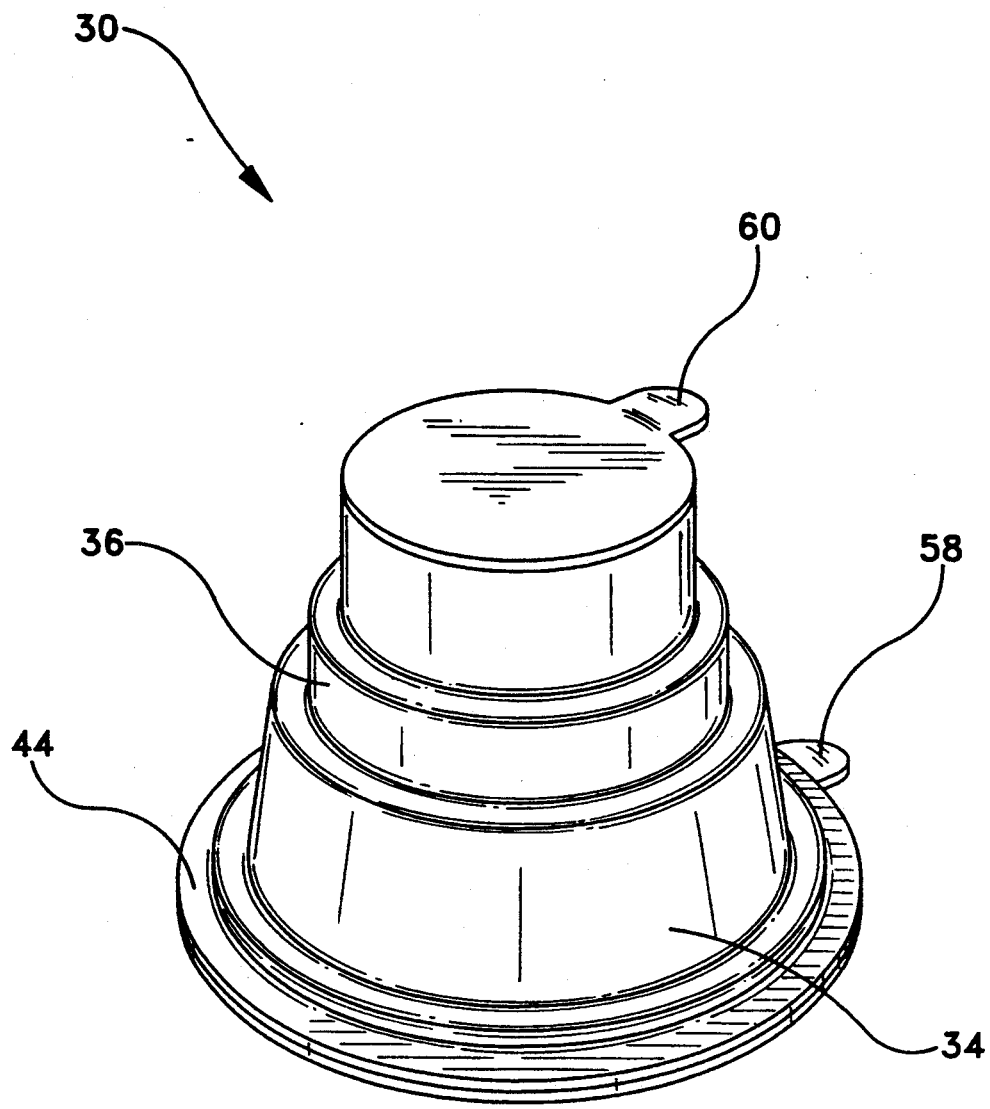
FIG. 3 is a perspective view of a trans-membrane co-culture system of the present invention.
Figure 4:
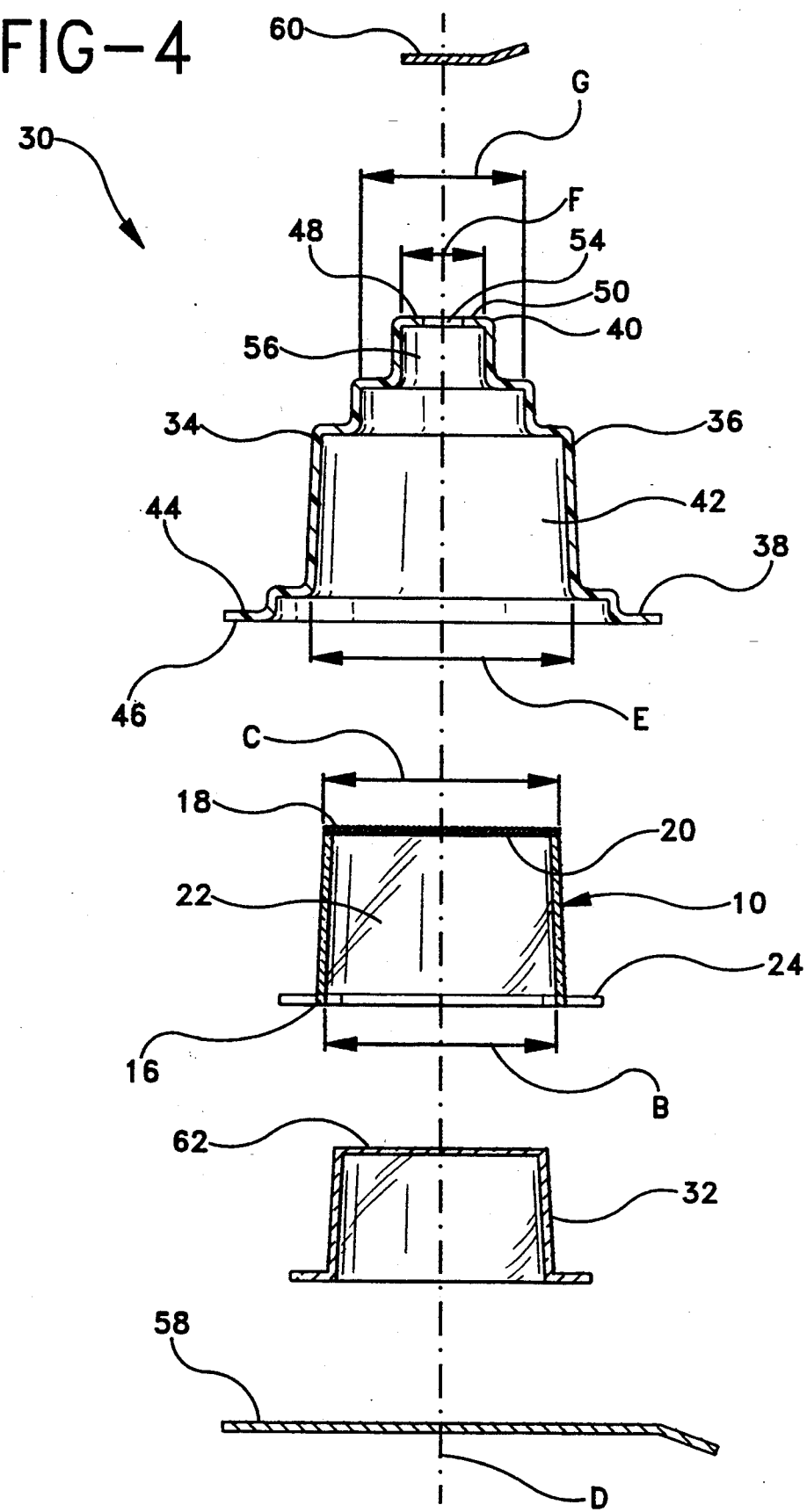
FIG. 4 is an exploded schematic view of the trans-membrane co-culture system of the present invention illustrated in FIG. 3.

Adverting to FIGS. 3 and 4, self-contained trans-membrane co-culture system 30 includes insert 10 as described hereinabove. The system further includes a plug 32 sized and placed to fit with an interference within well 22 to substantially obstruct fluid flow through membrane 20. System 30 also includes a housing 34 for containing insert 10 with plug 32 therein. Housing 34 includes an open tube 36 with a first end 38, a second end 40 and a passageway 42 therethrough. Housing 34 has a longitudinal axis "D" therethrough, a first diameter "E" at housing first end 38, a second diameter "F" at housing second end 40 and an intermediate diameter "G" between first end 38 and second end 40. Housing first end diameter "E" is larger than insert second end diameter "C". Housing intermediate diameter "G" and housing second end diameter "F" are smaller than insert second end diameter "C". Housing first end 38 has a flange 44 extending outwardly substantially perpendicular to axis "D" forming a surface. Housing second end 40 has a lip 48 extending inwardly substantially perpendicular to axis "D" forming a slip surface 50. Surface 50 has an opening 54 about axis "D". Housing 34 has a chamber 56 formed by coaxially placing second end 18 in housing first end 38 until insert second end 18 forms a substantially fluid tight fit at housing intermediate diameter "G" and flange 24 on insert 10 is contained within housing 34 at housing first end 38. Since housing intermediate diameter "G" is smaller than insert second end diameter "C", an interference fit exists between the insert and the housing to substantially ensure that chamber 56 is substantially fluid tight. Preferably, the interference between diameters "C" and "G" is between about 0.07 to about 0.13 mm.

Housing 34 may be formed from a polymeric material such as polyethylene terephthalate, glycol modified polyethylene terephthalate, polyethylene, polypropylene, polyvinylchloride and the like. Preferably housing 30 is formed by a sheet molding process from polypropylene PP-32 available from Rexene, Dallas, Tex.

The system includes a reclosable first lid 58 peelably bonded to first surface 46 substantially sealing first end 38 of the housing. The system further includes a reclosable second lid 60 peelably bonded to second surface 50 substantially sealing second end 40 of the housing. Lids 58 and 60 may be formed from any suitable fabric, paper or plastic sheet, but preferably are formed from a paper or spun bonded polyolefin that is permeable to gases and substantially impermeable to microorganisms. Tyvek 1073b from Dupont, Wilmington, Del. is a preferred spun bonded polyolefin. Lids 58 and 60 may be bonded to surfaces 46 and 50 respectively by any suitable adhesive, but preferably are adhesively bonded using a pressure sensitive adhesive such as a solvent based acrylic (preferably Minnesota Mining and Manufacturing No. 9457, St. Paul, Minn.) which is substantially free of extractable materials which may interfere with cell growth and additionally, readily peels and rebonds.

Plug 32 may be formed from a polymeric material sucy as polypropylene, polyethylene terephthalate, glycol modified polyethylene terephthalate, polyethylene, polyvinyl chloride and the like. Polypropylene PP-9234 (Rexene, Dallas, Tex.) is preferably sheet molded to form plug 32. Plug 32 has a surface 62 that is positioned adjacent membrane 20 when plug 32 is placed in well 22 of the insert. Preferably, plug surface 62 is concave with respect to the plug structure, so that when surface 62 is adjacent membrane 20 for substantially preventing fluid flow through the membrane, surface 62 is spared from contact with membrane 20.

Preferably, system 30 is exposed to an environment capable of rendering any microorganisms contained within the housing substantially non-viable. Such an exposure may include ionizing radiation or any known sterilant gas such as ethylene oxide and the like that does not adversely effect the materials used in the system. Since the housing is substantially sealed by lids that are substantially impermeable to microorganisms, the interior of the housing, the insert and the plug, are maintained substantially sterile after the sterilant exposure until removal of a lid. The design of the system allows opening and using chamber 56 for growing cells on one side of membrane 20 while well 22 of the insert, with plug 32 therein, is maintained substantially sterile as long as first lid 58 remains unopened.

Figure 5:
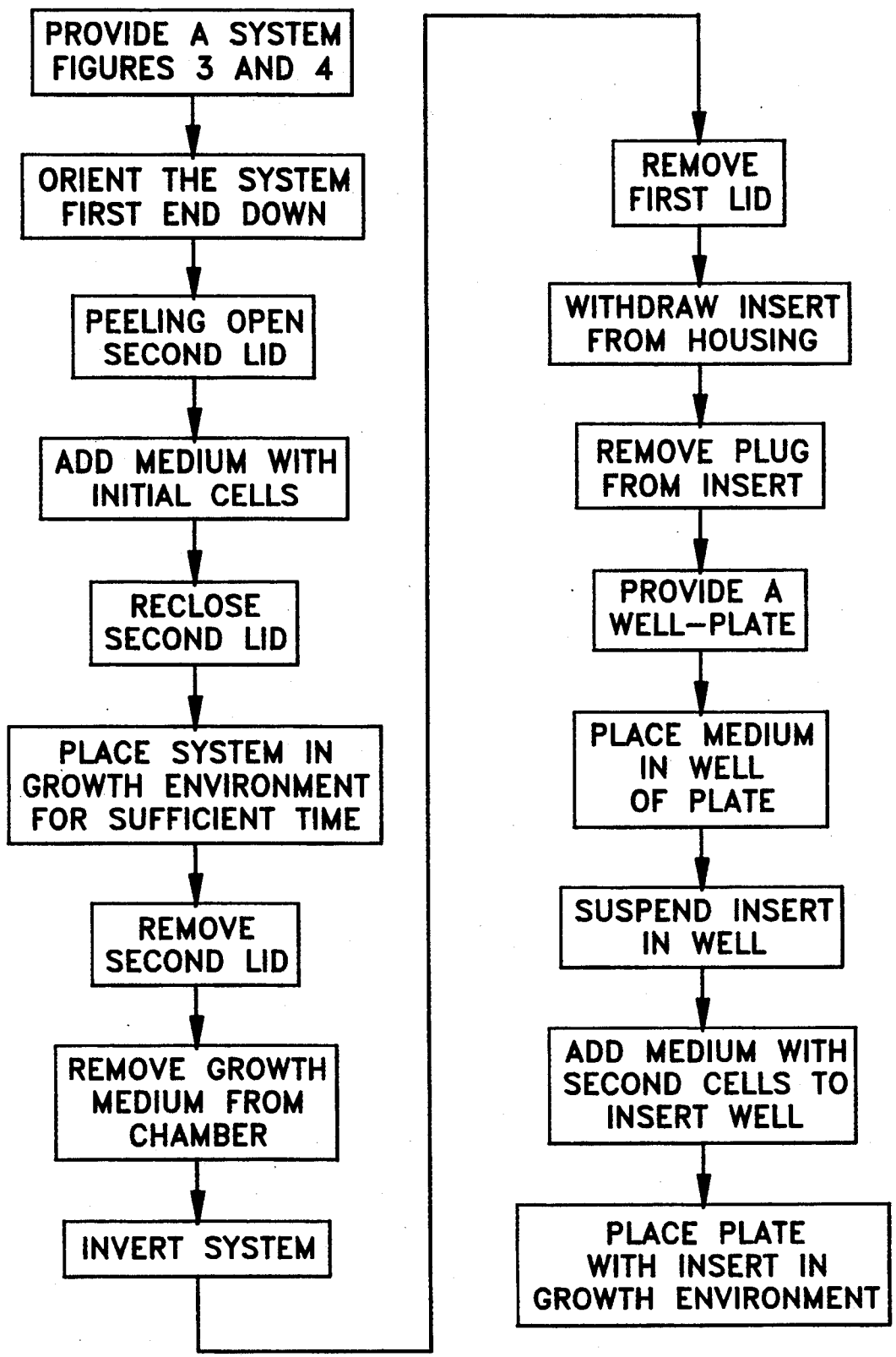
FIG. 5 is a flow chart of the method of using the system of present invention illustrated in FIGS. 3 and 4.

Referring to FIG. 5, a method for trans-membrane co-culture of cells includes providing system 30 of the present invention as described hereinabove. System 30 is placed so that first end 38 is down and second end 40 is up. Second lid 60 is then peeled open, thereby exposing chamber 56. A mixture including initial cells to be cultured and a sufficient quantity of a suitable growth medium is added to chamber 56 and second lid 60 is reclosed. The system with the cells and growth mixture in the chamber is then placed in an environment suitable for growing the initial cells. When sufficient cells have grown on the membrane, second lid 60 is removed and the growth medium is removed, leaving the initial cells on the membrane. The system is then inverted and first lid 58 is removed. Insert 10 with plug 32 therein is removed from the housing. Plug 32 is then removed. Alternatively, plug 32 may be removed from insert 10 while the insert is still within the housing, followed by the removal of the insert from the housing. A standard cell culture well plate, such as a is available from Falcon Labware, Franklin Lakes, N.J., is suitably sized for suspending the insert into a well on the plate, is then provided. A growth medium suitable for maintaining the initial cells is placed in the well of the plate in a sufficient quantity to cover the membrane when the insert is suspended in the well of the plate. The insert is suspended into the plate well using flange 24 so that the membrane with the initial cells on its surface contacts the initial cell growth medium. A mixture having secondary cells to be grown in a suitable growth medium is placed in well 22 of the insert. The plate with the suspended insert is then placed in a suitable environment for cell growth and the cells are allowed to grow.

The trans-membrane co-culture system of the present invention provides a ready-to-use substantially sterile cell culture study tool substantially free of cyto-toxic extractables. The system allows development of a population of initial cells on one side of insert membrane 20 while maintaining a substantially sterile environment on the well side of the membrane for growth of a second population of cells. The present invention provides a way for workers in cell culture to substantially improve their productivity and enhances their ability to conduct research.

What is claimed is:

1. A self contained trans-membrane co-culture system comprising:
    an insert comprising a tube with a passageway therethrough having a longitudinal axis, a sidewall substantially parallel to said axis connecting a first open end and a second end having a diameter, said second end having a microporous membrane bonded thereto substantially perpendicular to said axis for closing said second end and forming a well within said insert, said first end having a flange extending outwardly from at least a portion of said sidewall substantially perpendicular to said axis for suspending said insert;
    a removable plug sized and placed to fit with an interference within said well of said insert and substantially obstruct fluid flow through said microporous membrane;
    a housing for containing said insert having said plug therein, said housing including an open tube having a first end, a second end and a passageway therethrough, said housing having a longitudinal axis, a first diameter at said housing first end, a second diameter at said housing second end and an intermediate diameter between said housing first end and said housing second end, said housing first end diameter being greater than said insert second end diameter, said housing intermediate diameter and said housing second end diameter being less than said insert second end diameter, said housing first end having a flange extending outwardly substantially perpendicular to said housing longitudinal axis thereby forming a first surface, said housing second end having a lip extending inwardly substantially perpendicular to said housing longitudinal axis, said lip forming a second surface having an opening therethrough about said axis, said housing having a chamber formed by coaxially placing said second end of said insert in said housing first end until said insert second end forms a substantially fluid tight fit at said housing intermediate diameter and said flange on said insert is contained within said housing at said housing first end;
    first lid means for reclosably sealing said first end of said housing; and
    second lid means for reclosably sealing said second end of said housing.

2. The system of claim 1 wherein said first lid means and said second lid means are peelably bonded to said first surface and said second surface respectively using pressure sensitive adhesive and are formed from a material selected from the group consisting of paper and spun bonded polyolefin, said lid means providing a barrier for passage of microorganisms so that when said housing is sterilized, said insert having said plug and said chamber are maintained substantially sterile as long as said lid means are unopened.

3. The system of claim 1 wherein said housing is formed from a material selected from the group consisting of polypropylene, polyethylene terephthalate, glycol modified polyethylene terephthalate, polyethylene and polyvinylchloride.

4. The system of claim 1 wherein said plug is formed from a material selected from the group consisting of polypropylene, polyethylene, polyethylene terephthalate, glycol modified polyethylene terephthalate and polyvinylchloride.

5. The system of claim 1 wherein said sidewall of said insert is substantially rigid and is formed from a material selected from the group consisting of polyethylene terephthalate, polyethylene, polycarbonate and polystyrene.

6. The system of claim 1 wherein said insert tube is a frustum of a cone having a first diameter at said first end and a second diameter at said second end, said first diameter being larger than said second diameter.

7. The system of claim 6 wherein said sidewall forms an angle from parallel to said axis of less than about ten degrees.

8. The system of claim 1 wherein said microporous membrane is formed from a material selected from the group consisting of polyethylene terephthalate and polycarbonate, said membrane having open pores therethrough sized between about 0.2 to about 10.0 microns and a pore density between about $0.1 \times 10^6$ and about $100 \times 10^6$ pores per square centimeter.

9. The system of claim 1 wherein said plug when positioned in said well has a surface adjacent said membrane, said surface being generally concave so that said plug surface does not contact said membrane.

10. A method for trans-membrane co-culture of cells comprising:

providing a trans-membrane co-culture system comprising an insert having a longitudinal axis, a sidewall substantially parallel to said axis connecting a first open end and a second end having a diameter, said second end having a microporous membrane bonded thereto substantially perpendicular to said axis for closing said second end and forming a well within said insert, said first end having a flange extending outwardly from at least a portion of said sidewall substantially perpendicular to said axis for suspending said insert, a removable plug sized and placed to fit with an interference within said well of said insert and substantially obstruct fluid flow through said microporous membrane, a housing for containing said insert having said plug therein comprising an open tube having a first end, a second end and a passageway therethrough, said housing having a longitudinal axis, a first diameter at said housing first end, a second diameter at said housing second end and an intermediate diameter between said housing first end and said housing second end, said housing first end diameter being greater than said insert second end diameter, said housing intermediate diameter and said housing second end diameter being less than said insert second end diameter, said housing first end having a flange extending outwardly substantially perpendicular to said housing longitudinal axis thereby forming a first surface, said housing second end having a lip extending inwardly substantially perpendicular to said housing longitudinal axis, said lip forming a second surface having an opening therethrough about said housing axis, said housing having a chamber formed by coaxially placing said second end of said insert in said housing first end until said insert second end forms a substantially fluid tight fit at said housing intermediate diameter and said flange on said insert is contained within said housing at said housing first end, a first lid reclosably peelably bonded to said first surface of said housing substantially sealing said first end of said housing; and a second lid reclosably peelably bonded to said second surface of said housing sealing said second end of said housing;

placing said system with said housing first end down and said housing second end up;

peeling open said second lid thereby exposing said chamber;

adding a mixture with initial cells to be grown to said chamber with a sufficient quantity of a suitable growth medium;

reclosing said second lid;

placing said system in a suitable environment for cell growth;

allowing the initial cells to grow on said membrane;

removing said second lid;

removing said growth medium from said chamber leaving the initial cells on said membrane;

inverting said system;

removing said first lid;

withdrawing said insert from said housing;

removing said plug from said insert;

providing a well plate having a well suitable for suspending said insert from said insert flange;

placing a suitable growth medium in the well of said well plate;

suspending said insert into the well by said insert flange so that said growth medium contacts said membrane having the initial cells thereon;

adding a mixture with secondary cells to be grown to said well of said insert in a sufficient quantity of suitable growth medium;

placing said plate with said insert suspended therein in a suitable environment for cell growth; and allowing the cells to grow.

11. The method of claim 10 wherein said providing step includes providing a system which is substantially sterile until said lids are opened.

* * * * *